(12) United States Patent
Wöhrle et al.

(10) Patent No.: US 7,145,050 B2
(45) Date of Patent: *Dec. 5, 2006

(54) MODIFIED SUPPORTED METATHESIS CATALYSTS

(75) Inventors: Ingo Wöhrle, Holzminden (DE); Aurélia Reckziegel, Holzminden (DE); Peter Esser, Summerville, SC (US); Martin Stürmann, Leverkusen (DE)

(73) Assignee: Symrise GmbH & Co. KG, Holzminden (DE)

( * ) Notice: Subject to any disclaimer, the term of this patent is extended or adjusted under 35 U.S.C. 154(b) by 235 days.

This patent is subject to a terminal disclaimer.

(21) Appl. No.: 10/227,200

(22) Filed: Aug. 23, 2002

(65) Prior Publication Data

US 2003/0054956 A1  Mar. 20, 2003

(30) Foreign Application Priority Data

Aug. 28, 2001 (DE) .............................. 101 42 035

(51) Int. Cl.
*C07C 4/08* (2006.01)
*C07C 6/06* (2006.01)

(52) U.S. Cl. ............... 585/646; 585/647; 585/353; 585/354

(58) Field of Classification Search .......... 585/646, 585/647, 353, 354
See application file for complete search history.

(56) References Cited

U.S. PATENT DOCUMENTS 4,754,098 A * 6/1988 Drake .................. 585/646
5,898,092 A * 4/1999 Commereuc ............. 585/647
2003/0069460 A1* 4/2003 Wohrle et al. ........... 585/646
2003/0230598 A1* 12/2003 Kendall et al. .......... 222/145.6

FOREIGN PATENT DOCUMENTS

DE    197 27 256 A1   1/1999
GB    1 216 587       9/1968

OTHER PUBLICATIONS

J.C. Mol, Olefin Metathesis Over Supported Rhenium Catalysts, 1999, vol. 51, pp. 289-299, paragraphs 3.1.1, 3.1.3 and 03.2, no month.
J. Hietala et al, The Surface Acidity of Pure and Modified Aluminas in Re/A1203 Metathesis Catalysts as Studied by 1H MAS NMR Spectroscopy and Its Importance in the Ethenolysis od 1,5-Cyclooctadiene, 1984, vol. 150, pp. 46-55, examples 14-18, 21 and 22, table 1, pp. 26 and 47, no month.
Kawai et al, Metathesis of N-Alkenes Over a CsN03-Re207-A1203 Catalyst, 1988, vol. 46, pp. 157-172, p. 158, no month.
Xiaoding X et al., Re207/A1203.B203 Metathesis Catalyst, 1986, vol. 82, pp. 1945-1953, no month.

* cited by examiner

*Primary Examiner*—Elizabeth D. Wood
(74) *Attorney, Agent, or Firm*—Akerman Senterfitt; Stephan A. Pendorf

(57) ABSTRACT

The invention relates to modified supported catalysts based on $Re_2O_7/\gamma\text{-}Al_2O_3$ for use in the preparation of cycloalkadienes in a metathesis reaction, a process for preparing cycloalkadienes in the presence of these supported catalysts and the use of the resulting cycloalkadienes for the preparation of fragrances.

1 Claim, 1 Drawing Sheet

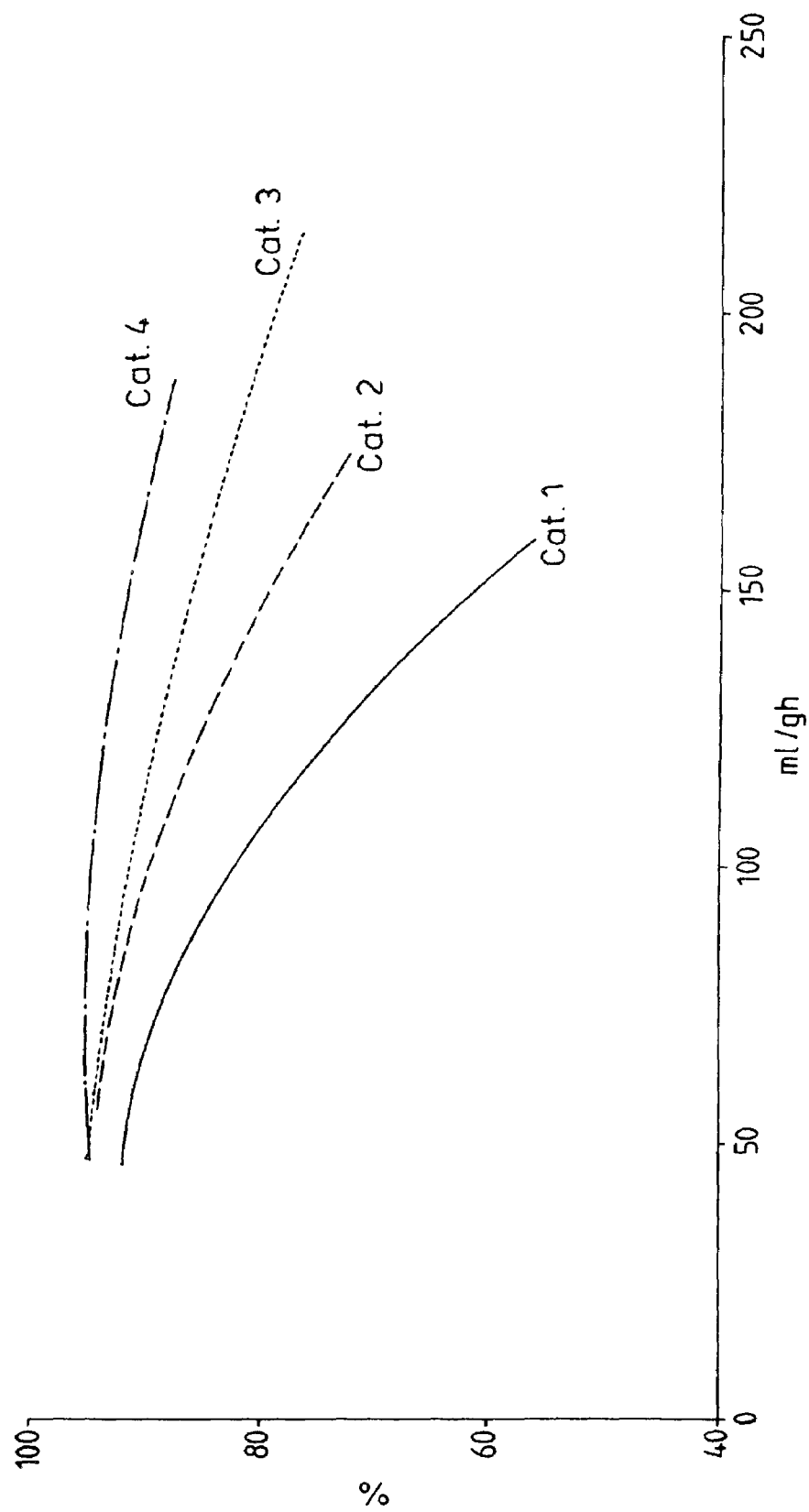

MODIFIED SUPPORTED METATHESIS CATALYSTS

FIELD OF THE INVENTION

The present invention relates to modified supported catalysts based on $Re_2O_7/\gamma\text{-}Al_2O_3$ for use in the preparation of cycloalkadienes in a metathesis reaction. The present invention also relates to a process for preparing cycloalkadienes in the presence of these supported catalysts and to the use of the cycloalkadienes produced.

Cycloalkenes, preferably cycloalkadienes having a ring size of from 12 to 18 carbon atoms, are used, inter alia, to prepare oxygen-containing, macrocyclic compounds. The compounds can be used in the preparation of macrocyclic ketones, lactones and epoxides, which are prized as musk fragrances in the perfume industry.

BACKGROUND OF THE INVENTION

EP-A 182 333 discloses that the catalyst system $Re_2O_7/\gamma\text{-}Al_2O_3/SnR_4$, where R is an alkyl radical, can be used in a metathesis reaction of highly dilute cycloolefin solutions in the liquid phase to give the corresponding cycloalkadienes.

The preparation of cycloalkadienes by a metathesis reaction of cyclooctenylenes having a degree of polymerization of greater than or equal to three and/or cycloalkamonoenes in the liquid phase in the presence of a supported catalyst based on $Re_2O_7/\gamma\text{-}Al_2O_3$ is described in EP-A 343 437.

Many modifications to supported catalysts based on $Re_2O_7/\gamma\text{-}Al_2O_3$, like the additions of dopants have been studied and described in the literature with the aim of improving these catalysts in respect of activity or operating life. The selectivity in respect of the cycloalkadienes to be formed and the total selectivity based on all desired metathesis products, i.e. the sum of desired cycloalkadienes and oligomeric and polymeric metathesis products, is likewise important. Metathesis products, which correspond to downstream products or by-products and are formed from the starting materials not according to plan. For example, ring sizes, which are smaller or larger by one, two or three carbon atoms, are not desired.

GB-1216587 discloses that impregnation of aluminum oxide with anions, for example, with phosphate ions, can increase the activity of the $Re_2O_7/\gamma\text{-}Al_2O_3$ metathesis catalyst.

Metathesis catalysts modified with cesium are known from *Journal of Catalysis* 1984, 89, 452, and *Journal of Molecular Catalysis* 1988, 46, 157.

The influence of the treatment of $Re_2O_7/\gamma\text{-}Al_2O_3$ metathesis catalysts with acids is discussed in *J. Chem. Soc., Faraday Trans.* 1, 1986, 82, 2707.

Due to the necessarily high dilution of the cycloolefin solutions used in the metathesis reaction, the amount of cycloalkadienes, which is obtainable per unit time, has been unsatisfactory from economic, engineering, and industrial points of view.

SUMMARY OF THE INVENTION

It is, therefore, an object of the present invention, to provide supported catalysts and processes by means of which a relatively large amount of cycloalkadienes can be obtained per unit time. It is also an object of the present invention, to achieve a higher productivity and a higher space-time yield in the metathesis process.

It has now been found that modification with phosphorus, cesium, mineral acids or combinations of these modifications can result in a significant increase in the activity and productivity of a supported $Re_2O_7/\gamma\text{-}Al_2O_3$ catalyst. This is particularly noticeable at relatively high space velocities, so that the amount of cycloalkadienes obtainable per unit time can be significantly increased. It is particularly advantageous that an excellent total selectivity based on all metathesis products can be achieved using the modified supported catalysts. Furthermore, it has been found that the supported catalysts of the present invention have a longer operating life, as a result of which more metathesis products and cycloalkadienes can be produced within a supported catalyst cycle. In addition, the supported catalysts have a longer total life.

BRIEF DESCRIPTION OF THE DRAWINGS

The Figure illustrates the cyclooctene-based conversion (in percent, y axis) as a function of the space velocity (in ml/gh, x axis) in a metathesis reaction using supported catalysts according to the present invention (Cat. 2 to 4) in comparison with a commercially obtainable swirl-strand supported catalyst Cat. 1.

DETAILED DESCRIPTION OF THE INVENTION

The present invention provides supported catalysts for use in the preparation of cycloalkadienes in a metathesis reaction, comprising a) $\gamma\text{-}Al_2O_3$ as a support material, b) from 1 to 12% by weight of $Re_2O_7$, c) from 0 to 40% by weight of $SnR_4$ or $SnO_2$ or a mixture of these tin compounds, where R is an alkyl radical having from 1 to 8 carbon atoms, and also, at least one dopant selected from d) phosphorus, e) cesium, and f) a mineral acid, where the % by weight are in each case based on the total weight of the catalyst.

The present invention further provides a process for preparing cycloalkadienes from cycloalkamonoenes, cyclopolyenes, acyclic polyenes or mixtures thereof by a metathesis reaction in the liquid phase in the presence of the above-mentioned supported catalysts, and provides for the use of the cycloalkadienes, which are obtainable according to the present invention, for the preparation of fragrances, preferably for the preparation of macrocyclic fragrances.

For the purposes of the present invention, the metathesis solution is the starting solution, i.e., a solvent containing at least one hydrocarbon selected from the group consisting of cycloalkamonoenes, cyclopolyenes, and acyclic polyenes.

Unless indicated otherwise, the % by weight are based on the total weight of the supported catalyst.

The dopants, active ingredients, coatings or treatments mentioned below can be applied to the supported catalyst by customary methods known to those skilled in the art, for example, impregnation.

The $Re_2O_7$ content of the supported catalyst, based on the weight of the supported catalyst, is in the range from 1 to 12% by weight, preferably in the range from 2 to 8% by weight, more preferably in the range from 3 to 6% by weight. The rhenium is usually applied by impregnation of the support material with an aqueous solution of one or more rhenium compounds and subsequent thermal treatment of the material, resulting in formation of $Re_2O_7$. Suitable rhenium compounds include perrhenates, such as ammonium perrhenate, perrhenic acid or rhenium heptoxide.

The supported catalyst can contain from 0.5 to 40% by weight, preferably from 1 to 20% by weight, more preferably from 1 to 10% by weight, of $SnR_4$ or $SnO_2$ or a mixture of these tin compounds, where R is an alkyl radical, having from 1 to 8 carbon atoms.

Preferred tin tetraalkyls include tetramethyltin, tetraethyltin, tetra-n-butyltin, tetra-n-octyltin; preferably, the tetraalkyl is tetramethyltin. Preferably, the supported catalyst is brought into contact with a solution containing a tin tetraalkyl, before commencement of the metathesis reaction, in which case, it is also possible to use mixtures of the tin tetraalkyls mentioned. Application of tin dioxide can be carried out, for example, in the regeneration of the supported catalyst containing a tin tetraalkyl, but can also be achieved by impregnating the supported catalyst with water-soluble tin compounds and subsequently heating it to 500–600° C. in an oxygen-containing atmosphere, resulting in formation of tin oxide.

Preferably, the supported catalysts of the present invention contain from 0.1 to 8% by weight, preferably, from 0.2 to 5% by weight. More preferably, from 0.3 to 3% by weight, of phosphorus, based on the total weight of the supported catalyst.

Doping of the supported catalyst with one or more phosphorus compounds can be carried out before or after application of the rhenium. Preference is given to treatment of the support material before treatment with a rhenium compound. Treatment is with an aqueous solution of phosphoric acid or phosphates, preferably ammonium phosphates, more preferably ammonium hydrogen phosphate.

Preferably, the supported catalysts of the present invention can contain from 0.1 to 6% by weight, preferably from 0.2 to 4% by weight. More preferably, from 0.3 to 2% by weight, of cesium, based on the total weight of the supported catalyst.

Doping of the supported catalyst with one or more cesium compounds can be carried out before or after application of the rhenium. Preference is given to treatment of the support material after treatment with a rhenium compound. Treatment with an aqueous solution of cesium salts, preferably, cesium halides, cesium nitrate, cesium phosphate, cesium acetate, particularly preferably, cesium chloride and cesium nitrate, is useful.

Preferably, the supported catalyst is treated with one or more mineral acids, either before or after application of the rhenium.

Preference is given to treating the $\gamma$-$Al_2O_3$ support material or the Re laden supported catalyst with an aqueous HCl solution.

It is also advantageous for the metathesis reaction to be carried out in the presence of a tin tetraalkyl. The tin tetraalkyls are typically added to the metathesis solution before commencement of the metathesis reaction, and this mixture is conveyed from a reservoir over the bed of supported catalyst. The tin tetraalkyls are typically added to the metathesis solution in an amount of from 0.1 to 8% by weight, preferably, from 0.1 to 5% by weight, more preferably, from 0.1 to 2.5% by weight, based on the weight of the supported catalyst. Preferred, tin tetraalkyls include tetramethyltin, tetraethyltin, tetra-n-butyltin, tetra-n-octyltin. Preference is given to tetramethyltin.

The supported catalysts typically have specific surface areas of from 100 to 300 $m^2/g$ determined by the BET method (Brunauer, Emmett and Teller method).

The supported catalysts are preferably used as shaped bodies, such as—hollow rods, extrudates, ram extrudates, spheres, cylinders, cubes, cones and the like. More preferably, the shaped bodies are spheres, swirl strands (SS) or cylinders.

Preference is given to a continuous reaction procedure, preferably a vertical arrangement of the supported catalysts in a fixed bed, with the metathesis solution being passed through the fixed bed from the bottom upwards.

The content of cycloalkamonoenes, cyclopolyenes, acyclic polyenes or mixtures thereof, in the liquid phase is typically in the range from 0.5 to 10 g/l. Preferably in the range from 1.0 to 5.5 g/l, and in particular in the range from 2.0 to 4.0 g/l.

The starting materials are used in metathesis-inert solvents. Suitable solvents include, for example, hydrocarbons and halogenated hydrocarbons, preferably butane, pentane, hexane, heptane, octane, cyclopentane, cyclohexane, cyclooctane, dichloromethane, trichloroethane. Preference is given to n-pentane, n-hexane, n-heptane, n-octane, isooctane, cyclopentane, cyclohexane; More preference is given to n-pentane and n-hexane. It is also possible to use mixtures of hydrocarbons, e.g. petroleum ether.

Advantageous cycloalkamonoenes are those having a ring size of from 4 to 12 carbon atoms. Preferred cycloalkamonoenes include cyclopentene, cyclohexene, cycloheptene, cyclooctene, cyclononene, cyclodecene and cyclododecene. More preference is given to cycloheptene and cyclooctene.

Useful cyclopolyenes or acyclic polyenes include those which can be obtained from the above mentioned cycloalkamonoenes. The cyclopolyenes or acyclic polyenes can, for example, be formed as by-products in metathetic dimerizations, by ring-opening metatheses or polymerizations. In general, the cyclopolyenes and the acyclic polyenes have a degree of polymerization from 3 to 50, preferably, one of from 3 to 20. For the purposes of the present invention, the degree of polymerization is the number of monomer units, identical or different, of which the polyene is composed.

Preferred cyclopolyenes for the purposes of the present invention include polymers or copolymers of the above mentioned cycloalkamonoenes, with the cyclopolyenes having a degree of polymerization of greater than or equal to 3, preferably from 3 to 50, more preferably from 3 to 20. Preference is given to using cyclopolyenes derived from cycloheptene, cyclooctene or their copolymers.

More preferred cyclopolyenes include cyclopolyoctenylenes of the formula

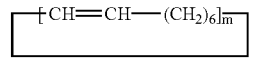

having a degree of polymerization m of at least 3, where m is preferably in the range from 3 to 50, more preferably in the range from 3 to 20.

Cycloalkamonoenes, cyclopolyenes, and acyclic polyenes can be present in the metathesis solutions in any compositions and mixing ratios. Preference is given to metathesis solutions containing cycloalkamonoenes. If metathesis solutions containing only cycloalkamonoenes as olefinic compounds are used, preference is given to cycloheptene, cyclooctene or mixtures thereof. Preference is also given to mixtures of cycloalkamonoenes and cyclopolyenes, with mixtures comprising cycloheptene, cyclooctene or a mixture thereof and cyclopolyheptenylene, cyclopolyoctenylene, copolymers of cycloheptene and cyclooctene or a mixture thereof being more preferred.

If mixtures of cycloalkamonoenes and cyclopolyenes are used, the preferred weight ratio is in the range 0.1–2:1, more preferably in the range 0.2–1:1.

Most preference is given to a mixture of cyclooctene and cyclopolyoctenylene, in which case a ratio of cyclooctene to cyclopolyoctenylenes in the range 0.25–0.5:1 is most preferred.

If cycloalkamonoenes or mixtures containing cycloalkamonoenes are used in the metathesis reaction, it is advantageous to set a conversion, based on the content of cycloalkamonoenes, in the range from 40 to 99%, preferably in the range from 50 to 95%, more preferably in the range from 60 to 85%.

The metathesis solution can also contain small proportions of cycloalkadienes, preferably cycloalkadienes to be formed, i.e. product cycloalkadienes. These can be present in small amounts in the cycloalkamonoenes, cyclopolyenes or the acyclic polyenes and result from, for example, distillation.

Preferred cycloalkadienes, which can be prepared by the process of the present invention include those having from 12 to 18 carbon atoms. More preferred cycloalkadienes include 1,8-cyclotetradecadiene, 1,8-cyclopentadecadiene, and 1,9-cyclohexadecadiene. Most preferred is 1,9-cyclohexadecadiene.

The metathesis reaction can be carried out at temperatures in the range from 0 to 100° C., preferably at a temperature in the range from 25 to 80° C., more preferably one in the range from 35 to 600° C.

When using solvents, whose boiling point is below the reaction temperature, the reaction can also be carried out under a range of pressure. In general, the metathesis reaction can be carried out at a pressure in the range from 1 to 10 bar.

The preparation and doping of the supported catalysts to be used is carried out by methods known to those skilled in the art. It is usually carried out by impregnation of the support material with an aqueous solution containing a compound of the doping element or of the material to be applied and subsequent drying and/or thermal treatment of the material. Thermal treatment of the supported catalyst is carried out in a temperature range from 200 to 600° C., with the maximum usable temperature being in the region of about 600° C.

After use in the metathesis reaction, the supported catalyst can be regenerated and reused for the metathesis reaction. As described, for example, in EP-B1-991 467, the supported catalyst can be removed from the metathesis reactor, washed with a metathesis-inert solvent and subsequently dried. Thermal treatment of the supported catalyst in the regeneration is carried out in a temperature range from 200 to 600° C., with the maximum usable temperature being about 600° C. The thermal treatment is carried out in an oxygen-containing atmosphere, for example, air, which can, if desired, be additionally admixed with inert gases, such as nitrogen or argon.

EXAMPLES

The following examples illustrate the present invention:

Example 1

Preparation of Cat. 2

250 g of γ-aluminum oxide in the form of swirl strands (procured from KataLeuna) are impregnated with a solution comprising 25 g of diammonium hydrogen phosphate and 1 l of distilled water at 80° C. for 6 hours, filtered, washed with 1 l of distilled water, dried and calcined at 580° C. for 18 hours. This material is subsequently impregnated with 130 ml of an aqueous solution of 17 g of ammonium perrhenate and dried. After treatment at 500–580° C. in a stream of air for two hours, the catalyst was kept at the same temperature in a stream of nitrogen for a further 2 hours and, subsequently, cooled to room temperature. This gave additional 267.9 g of a supported catalyst (Cat. 2) containing 3.6% by weight of $Re_2O_7$ and 1.1% by weight of phosphorus.

Example 2

Preparation of Cat. 3

241 g of γ-aluminum oxide in the form of swirl strands (procured from KataLeuna) were impregnated with 125 ml of a solution of 9 g of rhenium oxide in water, and subsequently, dried. After treatment at 500–580° C. in a stream of air for two hours, the catalyst was kept at the same temperature in a stream of nitrogen for an addiitonal 2 hours and, subsequently, cooled to room temperature. After impregnation with 125 ml of an aqueous solution of 1.83 g of cesium nitrate, the catalyst was dried at 120° C. for two hours, followed by treatment at 500° C. in a stream of air for two hours, and cooling in a stream of nitrogen. This gave 244.4 g of supported catalyst containing 3.7% by weight of $Re_2O_7$ and 0.5% by weight of cesium.

Example 3

Preparation of Cat. 4

235 g of γ-aluminum oxide in the form of swirl strands (procured from KataLeuna) were impregnated with 244 ml of an aqueous solution of 16.6 g of ammonium perrhenate. Impregnation was carried out in two steps, using 122 ml of aqueous ammonium perrhenate solution each time, with subsequent drying in each case. After a second impregnation with 122 ml of an aqueous solution of 2.26 g of hydrogen chloride, the catalyst was dried, treated at 500–580° C. in a stream of air for two hours and treated at the same temperature in a stream of nitrogen for an additional 2 hours. After cooling under nitrogen, 243.3 g of catalyst (Cat. 4) containing 3.6% by weight of $Re_2O_7$ were obtained.

Example 4

Commercially Available Cat. 1

Cat. 1 is a commercially available catalyst and was procured from KataLeuna (Re content: 3.6% by weight of $Re_2O_7$ on γ-aluminum oxide).

The length of the swirl strands (SS) was typically in the range from 10 to 19 mm.

50 g of one of the supported catalysts described in Examples 1 to 3 (Cat. 2 to Cat. 4) or the commercially available catalyst Cat. 1 were in each case placed in a vertical tube reactor (height: 50 cm, diameter: 1.5 cm) under a protective gas atmosphere (argon). A solution containing 2.5% by weight of tetramethyltin (based on the weight of the supported catalyst) in n-hexane was circulated by means of a pump through the fixed bed of supported catalyst from the bottom upward at 25° C. for 3 hours. A solution containing 2.4 g of cyclooctene and 0.3% by weight of tetramethyltin, (based on the weight of supported catalyst) per liter of n-hexane was then passed continuously through the bed of supported catalyst from the bottom upward at 45° C. and atmospheric pressure.

The amount of metathesis solution passed over the bed of supported catalyst per unit time, i.e., the space velocity, was varied by means of the pump output.

The selectivity to 1,9-cyclohexadecadiene over the entire reaction was 36–38%. The selectivity to 1,9-cyclohexadecadiene and cyclopolyoctenylenes was about 99%.

As illustrated in graphical form in the Figure, the cyclooctene-based conversion (in percent, y-axis) as a function of the space velocity (in ml/gh, x-axis) in a metathesis reaction using the supported catalyst Cat. 2 to 4 in comparison with a commercially available swirl-strand supported catalyst Cat. 1. The supported catalysts of the invention Cat. 2 to 4 display a significantly higher activity, as a result of which a higher space-time yield and a higher productivity for cycloalkadienes can be achieved.

Although the invention has been described in detail in the foregoing for the purpose of illustration, it is to be understood that such detail is solely for that purpose and that variations can be made therein by those skilled in the art, without departing from the spirit and scope of the invention, except as it may be limited by the claims.

What is claimed is:

1. Process for preparing cycloalkadienes comprising the step of metathesizing cycloalkamonoenes, cyclopolyenes, acyclic polyenes or mixtures thereof in the liquid phase in the presence of a supported catalyst comprising:
   a) $\gamma$-$Al_2O_3$ as a support material,
   b) from 1 to 12% by weight of $Re_2O_7$
   c) from 0 to 40% by weight of $SnR_4$, $SnO_2$ or a mixture thereof, wherein R is an alkyl radical having from 1 to 8 carbon atoms, wherein that supported catalyst is modified by:
   d) at least one dopant selected from the group consisting of phosphors and cesium, and/or
   e) treatment with at least one mineral acid, wherein the % by weight are based on the total weight of the catalyst.

* * * * *